Figure 1:
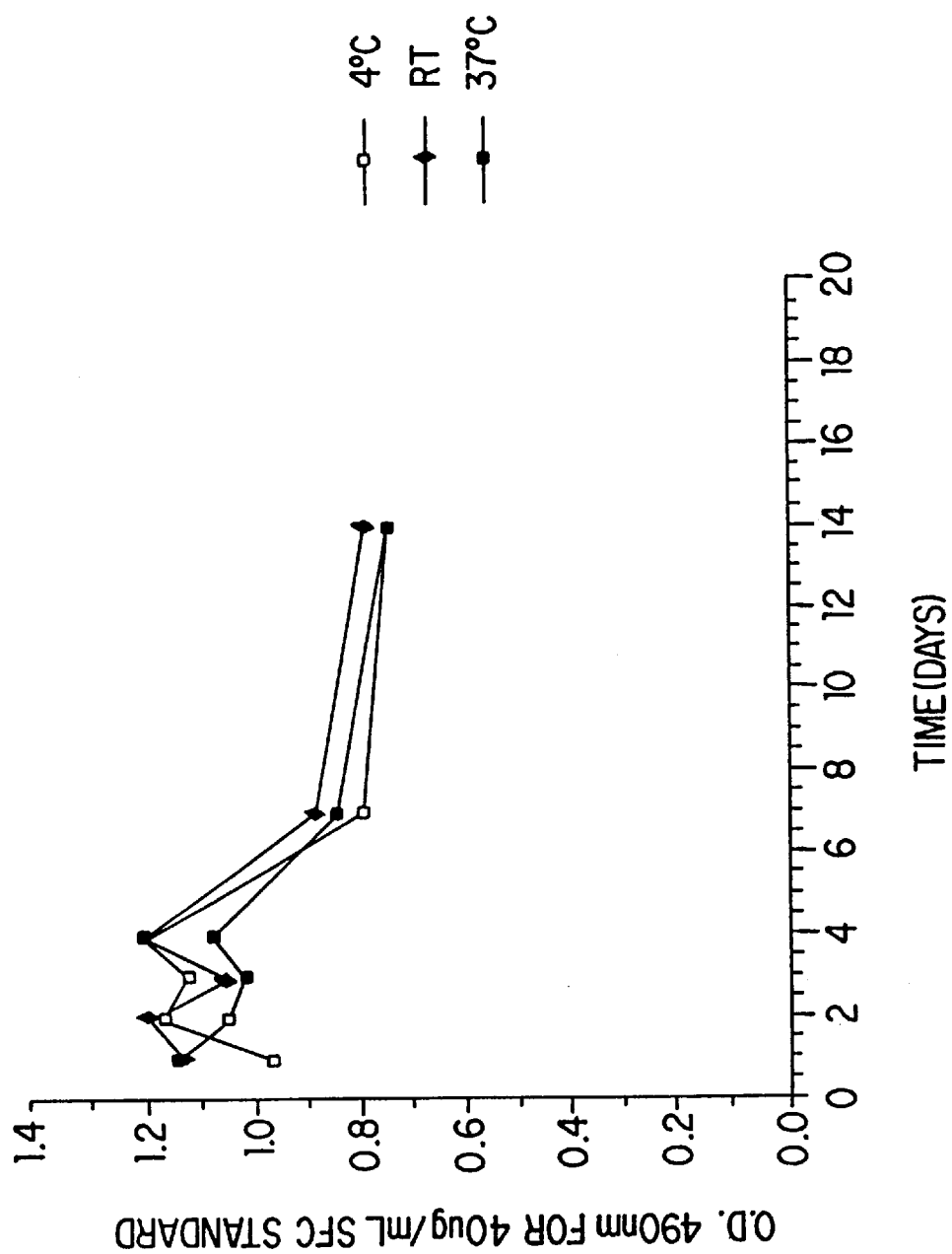

United States Patent [19]
Gargan et al.

[11] Patent Number: 5,837,540
[45] Date of Patent: Nov. 17, 1998

[54] METHOD OF PRODUCING FIBRIN-SPECIFIC ANTIBODIES USING SOLUBLE FIBRIN POLYMERS AS AN IMMUNOGEN

[75] Inventors: Paul E. Gargan, Granger; David G. M. Carville, Mishawaka, both of Ind.; Nada Dimitrijevic, Belgrade, Yugoslavia

[73] Assignee: American Biogenic Sciences, Inc., Copiague, N.Y.

[21] Appl. No.: 672,611

[22] Filed: Jun. 28, 1996

Related U.S. Application Data

[60] Provisional application No. 60/000,765, Jun. 30, 1995.
[51] Int. Cl.$^6$ .......................... A61K 39/00; C12N 15/06; C12N 5/16; C07N 16/36
[52] U.S. Cl. .................. 435/337; 424/184.1; 435/172.2; 435/328; 435/346; 530/388.25; 530/389.3; 436/547; 436/548
[58] Field of Search ..................................... 435/337, 328, 435/346, 172.2; 530/388.25, 389.3; 424/184.1; 436/547, 548

[56] References Cited

U.S. PATENT DOCUMENTS

| | | | |
|---|---|---|---|
| 4,957,903 | 9/1990 | Ranby | 514/18 |
| 5,091,512 | 2/1992 | Gargan et al. | 530/387 |

OTHER PUBLICATIONS

Schielen, WJ et al. Proc. Nat. Acad. Sci. USA. 86: 8951–8954, Nov. 1989.
Bini, A et al. Laboratory Investigation. 60(6): 814–821, Jun. 1989.
Kudryck, B. Molec. Immunol. 21(1): 89–94, Jan. 1984.
Gussow, F and Seeman, G. Meth. Enzymol. 203: 99–121, 1991.
Rotker, J et al. Eur. J. Biochem.. 155(3): 583–588, Mar. 1986.

*Primary Examiner*—David Saunders
*Assistant Examiner*—F. Pierre VanderVegt
*Attorney, Agent, or Firm*—Pennie & Edmonds LLP

[57] ABSTRACT

The subject invention relates to a method for producing antibodies using as an immunogen a composition comprising soluble crosslinked DesAABB fibrin polymers and soluble non-crosslinked DesAABB fibrin polymers. The invention provides a method for producing fibrin-specific antibodies which, for the purposes of the present invention, are defined as antibodies that specifically bind to soluble crosslinked DesAABB fibrin polymers and soluble non-crosslinked DesAABB fibrin polymers, but which do not specifically bind to: (a) fibrinogen, (b) plasmin-derived fibrinogen degradation products, (c) DesAA fibrin monomers, (d) DesAA fibrin polymers, (e) DesAABB fibrin monomers, (f) crosslinked fibrinogen, (g) DesAA fibrin monomer-fibrinogen complex, and (h) plasmin-derived fibrin degradation products.

12 Claims, 2 Drawing Sheets

METHOD OF PRODUCING FIBRIN-SPECIFIC ANTIBODIES USING SOLUBLE FIBRIN POLYMERS AS AN IMMUNOGEN

This application claims benefit of provisional application Ser. No. 60/000,765, filed Jun. 30, 1995.

1. FIELD OF THE INVENTION

The subject invention relates to a method for producing antibodies using as an immunogen a composition comprising soluble crosslinked DesAABB fibrin polymers and soluble non-crosslinked DesAABB fibrin polymers. The invention provides a method for producing fibrin-specific antibodies which, for the purposes of the present invention, are defined as antibodies that specifically bind to soluble crosslinked DesAABB fibrin polymers and soluble non-crosslinked DesAABB fibrin polymers, but which do not specifically bind to: (a) fibrinogen, (b) plasmin-derived fibrinogen degradation products, (c) DesAA fibrin monomers, (d) DesAA fibrin polymers, (e) DesAABB fibrin monomers, (f) crosslinked fibrinogen, (g) DesAA fibrin monomer-fibrinogen complex, and (h) plasmin-derived fibrin degradation products. The subject invention further provides fibrin-specific antibodies, which can be produced according to the method of the invention. The subject invention also provides for the use of fibrin-specific antibodies produced according to the method of the invention in an immunoassay and kit for in vitro detection of soluble crosslinked DesAABB fibrin polymers and soluble non-crosslinked DesAABB fibrin polymers.

2. BACKGROUND OF THE INVENTION

The hemostatic mechanism is a complex physiological response mechanism involved in repairing damage to a ruptured blood vessel. Hemostasis is achieved through the cooperative interactions among the wall of the damaged blood vessel, the platelets and the coagulation system. The role of the coagulation system is to provide an extensive insoluble fibrin network to stabilize and anchor the platelet plug which has been assembled on the subendothelial structure of the damaged vessel. The formation of the insoluble fibrin matrix from circulating fibrinogen is the result of a complex sequence of biochemical reactions culminating in the activation of thrombin at the required site. Coagulation is an amplification process involving a cascade of enzymatic reactions in which proenzymes (clotting factors) are activated sequentially to active enzymes. There are a number of physiological mechanisms controlling the fibrin polymerization process involved in thrombus formation. These include the thrombin inhibitor antithrombin III (ATIII), protein C, prostacyclin and various components of the fibrinolytic system such as tissue plasminogen activator (t-PA) and its fast acting inhibitor (PAI).

The homeostasis hypothesis proposed by Astrup in 1956 (Astrup, T., *Blood*, 11:781–806 (1956)) states than an equilibrium exists between fibrin formation (coagulation) and fibrin dissolution (fibrinolysis). In the normal or healthy state these functions are evenly balanced. However, when the hemostatic process is impaired, coagulation and fibrinolysis are pathologically expressed as thrombosis and hemorrhage, respectively. The clinical manifestations of pathological thrombosis or thrombotic disease are extremely diverse and include disseminated intravascular coagulation (DIC), deep vein thrombosis (DVT), arterial and venous thrombosis. Thromboembolism and thrombotic complications of other vascular disease, e.g., atherosclerosis, can result in occlusion of major arteries leading to organ ischemia and the attendant life-threatening conditions such as cerebrovascular accident (stroke), myocardial infarction, etc.

The fibrinolytic process involves the conversion of an inactive zymogen, plasminogen, to the proteolytic enzyme, plasmin, through the action of agents known as plasminogen activators. The molecular mechanism of physiological fibrinolysis is not fully understood, but it is known that during fibrin formation plasminogen binds to fibrin where it can be activated by plasminogen activators, e.g., t-PA. In this manner plasmin generation proceeds within the thrombus where it is protected from inactivation by the main physiological inhibitor of plasmin, alpha$_2$-antiplasmin.

Upon exposure to plasmin, fibrinogen and fibrin are digested down to their degradation products. Fibrinogen breaks down into fragments X and Y, and upon further exposure to plasmin, fragments D and E. Fibrin breaks down to fragments X, Y, D and E from non-crosslinked fibrin and crosslinked D-dimer, D-D/E complex, Y dimer, Y-D-dimer and X oligomer from crosslinked fibrin.

Assays for markers of thrombotic disorders have been conducted until quite recently using polyclonal antibodies in both radioimmunoassays and latex agglutination type assays. These assays have been demonstrated to be extremely unreliable by Gaffney (Gaffney, P. J., *Ann. N.Y. Acad. Sci.*, 408:407–423 (1983)). More specific and sensitive immunoassays (such as ELISAs) using monoclonal antibodies are becoming common practice in clinical laboratories. The limiting factor in these diagnostic assays is the specificity and affinity of the particular monoclonal antibody employed. The generation of highly specific antibodies, whether polyclonal or monoclonal, to any of the potential indicators of impaired hemostasis is hampered by both low levels of indicators and the antigenic relatedness of the particular marker with its precursor, which is normally present at much higher levels in plasma. Examples are the formation of complexes between enzymes and their inhibitors, e.g., thrombin-antithrombin III, plasmin-alpha$_2$-antiplasmin, t-PA-PAI-1. The number of new antigenic sites generated by such complex formation is extremely small and makes the production of immunological probes (such as monoclonal antibodies) difficult.

Likewise, a major problem associated with the acquisition of an antibody specific to fibrin, whether monoclonal or polyclonal, has been the structural and conformational similarities between fibrin and its physiological precursor fibrinogen. It has been estimated that the conservation of covalent structure when fibrinogen is converted to fibrin is greater that 98% (Plow, E. F., et al., *Semin. Thromb. Haemostas*, 8:36 (1982)) and, therefore, only a small percentage of the epitopes on the fibrin molecule are, in fact, neoantigens (and unique to fibrin).

Many of the approaches which have been adopted to acquire fibrin antibodies have concentrated on immunizing animals with soluble fibrin fragments and synthetic peptides which mimic exposed neoantigenic sites on fibrin. See Hui, K. Y., et al., *Science*, 22:1129–32 (1983); Scheefers-Borchel, V., et al., *Proc. Natl. Acad. Sci USA*, 82:7091–95 (1985); Elms, M. J., et al., *Thromb. Haemostas*, 50:591–94 (1983); and Kudryk, B., et al., *Mol. Immul.*, 21:89–94 (1984). However, soluble fibrin fragments and synthetic peptides may be chemically or conformationally unstable, either degrading or converting to insoluble form. As a result, these fragments or peptides may be chemically or conformationally changed during preparation or during the immunization process and, thus, they may no longer present a fibrin-unique epitope to the immune system of the animal in which they are injected.

3. SUMMARY OF THE INVENTION

The subject invention encompasses a method for producing fibrin-specific antibodies which utilizes as an immunogen a composition comprising soluble crosslinked DesAABB fibrin polymers and soluble non-crosslinked DesAABB fibrin polymers. Preferably, the soluble crosslinked DesAABB fibrin polymers and soluble non-crosslinked DesAABB fibrin polymers comprising the immunogen are stabilized so as to inhibit degradation or the conversion of the polymers to an insoluble clot. The stabilization of the polymers may be carried out by any technique known in the art, but is preferably carried out by combining the polymers of the invention with a stabilizing buffer. It is believed that such immunogen increases the ability to produce fibrin-specific antibodies. The immunogen can preferably be used to immunize any type or species of animal. However, use of the immunogen in conjunction with the enhanced immunological sensitivity of a germfree or antigen-free (AF) animal is preferred.

4. BRIEF DESCRIPTION OF THE FIGURES

FIG. 1. Stability study of the stabilized composition comprising soluble crosslinked DesAABB fibrin polymers and soluble non-crosslinked DesAABB fibrin polymers prepared, lyophilized, and reconstituted to 40 $\mu$g/ml as described, and stored in reconstituted form at 4° C., 22° C. (RT), or 37° C. for up to 14 days. Stability was determined at days 1, 2, 3, 4, 7 and 14 post-reconstitution by measuring immunoreactivity of the solution against monoclonal antibody MH1 using a standard ELISA formal and reading $OD_{490}$. The calibrator prepared according to the invention used a buffer in which 5% sucrose (w/v) was the stabilizing agent.

Figure 2:
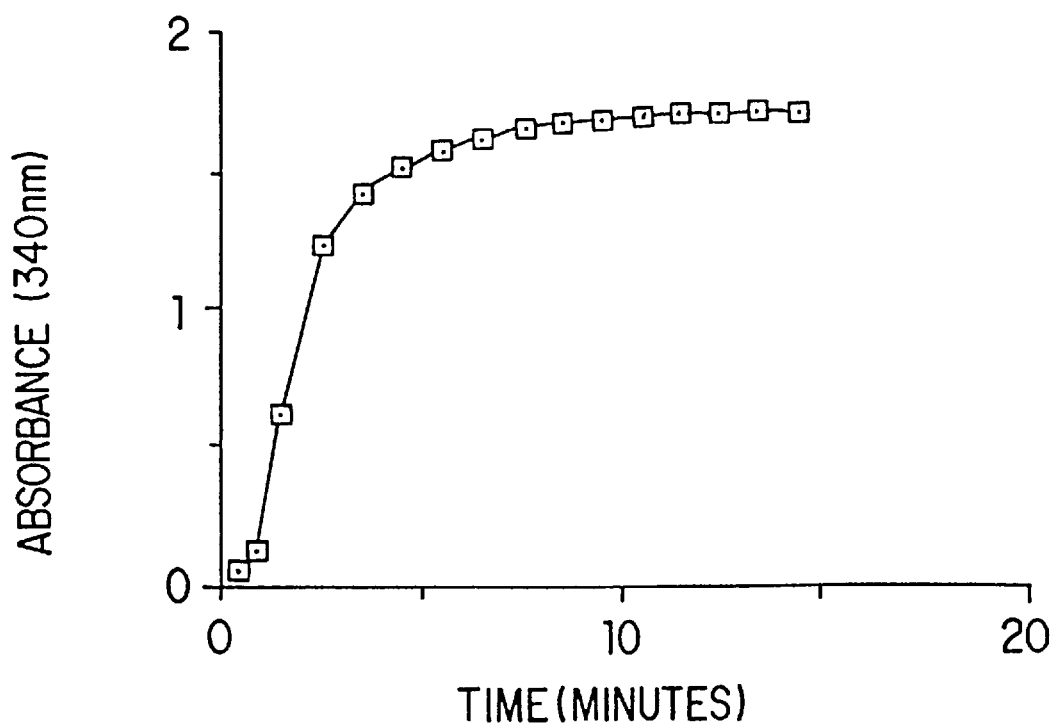

FIG. 2. The formation of DesAA fibrin by batroxobin treatment of plasma fibrinogen.

5. DETAILED DESCRIPTION OF THE INVENTION

5.1. THE IMMUNOGEN

The immunogen of the invention is a composition comprising soluble crosslinked DesAABB fibrin polymers and soluble non-crosslinked DesAABB fibrin polymers. Preferably, the soluble crosslinked DesAABB fibrin polymers and soluble non-crosslinked DesAABB fibrin polymers are stabilized so as to inhibit degradation or the conversion of the polymers to an insoluble clot. The stabilization of the polymers can be carried out by any technique known in the art, but is preferably carried out by combining such polymers with a stabilizing buffer.

Stability of the polymers of the composition may be determined by any method known in the art. For example, the stability of the composition may be determined immunologically by measuring the amount of immunocomplex formed between the composition and a fibrin-specific antibody, such as monoclonal antibody MH1 produced by hybridoma ATCC HB 9739, which is disclosed in U.S. Pat. No. 5,091,512 to Gargan et al. The amount of immunocomplex may then be determined by any technique known in the art. As disclosed in U.S. Pat. No. 5,091,512, the monoclonal antibody MH1 was raised by immunizing AF mice with a saline dispersion of a freeze-fractured fibrin preparation.

The following protocol describes a series of experiments that were carried out to determine how to produce a chemically stabilized fibrin preparation that it is believed will more effectively serve to produce fibrin-specific antibodies.

First, soluble crosslinked DesAABB fibrin polymers and soluble non-crosslinked DesAABB fibrin polymers were prepared and their immunoreactivity tested as follows. Fibrinogen (Enzyme Research Laboratories (ERL), South Bend, Ind.; free of plasminogen, Von Willebrand factor and fibronectin) was diluted in 0.06M TRIS/0.3M NaCl buffer, pH 7.4, to concentrations ranging from 1 to 10 mg/ml. Bovine thrombin (ERL) was added to the fibrinogen solution to final concentrations ranging from 0.005 to 0.05 NIH units/ml. Fibrinogen solutions were incubated for time periods ranging from 1 to 4 hrs. at 37° C. Following incubation, thrombin activity was stopped with the addition of PPACK (D-phe-pro-arg chloromethyl-ketone, dihydrochloride; Calbiochem™ Corp, San Diego, Calif.) ($10^{-7}$ to $10^{-3}$M final concentration), or hirudin (5 antithrombin units (ATU)/ml).

Samples from each solution were stored at different temperatures, including at −80° C., −20° C., 4° C., 22° C., and 37° C., for varying lengths of time. The immunoreactivity of each solution was then tested against monoclonal antibody MH1 using a standard ELISA format.

Accordingly, soluble crosslinked DesAABB fibrin polymers and soluble non-crosslinked DesAABB fibrin polymers was detected using a sandwich type enzyme-linked immunoassay system. The capture antibody in the current invention was monoclonal antibody MH1. The detection (tag) antibody was a HRP conjugate of the antifibrinogen antibody 45J, ATCC HB 9740.

Polystyrene microtitre plates (96-well; Maxisorp. Nunc Immunoplates, VWR) were coated with monoclonal antibody MH1 by incubation of a 100 $\mu$l solution of the Mab (at 5 $\mu$g/ml) in coating buffer (PBS, pH 7.4) for 12–16 hrs. at 4° C. Unbound antibody was removed from the plates by washing the wells three times with a solution of PBS-TWEEN™ dispersant. The MH1-coated wells were post-coated with BSA by incubating a 200 $\mu$l solution of BSA (0.5%) in 0.06M Tris/0.3M Nacl/5% sucrose for 2 hrs. at 22° C. Unbound BSA was removed by inverting the plates and tapping gently onto a paper towel. Citrated samples (50 $\mu$l) containing soluble fibrin polymers were incubated on the MH1-BSA blocked wells for 30 min. at 22° C. Unbound material was removed by inversion and gentle tapping of the microtitre plates. The wells were then washed three times with a solution of PBS-TWEEN™ dispersant. Bound soluble fibrin was detected by first incubating 100 $\mu$l of Tris/BSA/sucrose solution of the 45J-HRP conjugate in the wells for 30 min. at 22° C. Unbound conjugate was removed by inverting the plate and washing the wells 3 times with a solution of PBS-TWEEN™ dispersant. The bound conjugate was detected by addition of 100 $\mu$l of O-phenylenediamine dihydrochloride solution for 10 min. at room temperature. The substrate solution was prepared by dissolving a tablet of O-phenylenediamine dihydrochloride in a sodium citrate solution containing $H_2O_2$.

The colorimetric reaction was quenched after 10 min. by addition of a 50 $\mu$l solution of $H_2SO_4$ (1M). The absorbance of the solution in each well was determined at 490 nm in a Thermomax microtitre plate reader (Molecular Devices, Menlo Park, Calif.).

The results of these experiments demonstrate that samples of soluble fibrin polymers kept at 4° C., 22° C. and 37° C. were unstable after more than a week in storage, losing substantially all of their immunoreactivity. Samples kept at −20° C. and −80° C. retained immunoreactivity against MH1 for up to 3 months. Once thawed, and then stored at 4° C., 22° C. or 37° C., the samples initially stored at −20° C. or −80° C. lost significant immunoreactivity within 24 hrs.

A series of experiments was performed to determine how to produce chemically stabilized soluble fibrin polymer composition. As a result of these experiments, and using a modification of the method of Smith (1980), *Biochem. Jour.*, 185:1–11, a stabilized fibrin polymer composition was produced. In a first step, soluble crosslinked DesAABB fibrin polymers and soluble non-crosslinked DesAABB fibrin polymers were prepared enzymatically from fibrinogen. In a second step, this soluble fibrin polymer preparation was stabilized by dilution in a stabilizing buffer followed by lyophilization.

A solution of soluble crosslinked and soluble non-crosslinked DesAABB fibrin polymers may be prepared by any method known in the art. For example, fibrinogen (ERL) is diluted in 0.06M TRIS/0.3M NaCl buffer, pH 7.4, to a final concentration of about 4.4 mg/ml and to a final volume of about 10 ml. Bovine thrombin (ERL) is added to the fibrinogen solution to result in a final concentration of about 0.005 NIH units/ml. The solution is incubated for a sufficient time, for example, between 2 to 3 hrs., to form a solution of soluble crosslinked DesAABB soluble fibrin polymers and soluble non-crosslinked DesAABB fibrin polymers. Thrombin activity is quenched by adding, for example, about 100 µl of PPACK ($10^{-5}$M final concentration).

A buffer containing a stabilizing agent is then prepared. A stabilizing agent is any agent added to a solution of soluble crosslinked DesAABB fibrin polymers and soluble non-crosslinked DesAABB fibrin polymers that increases the immunoreactive stability of the polymers when lyophilized and also when reconstituted.

Stabilizing agents which may be useful to practice the invention include: osmolytic stabilizers, including, but not limited to, polyols and sugars, such as, for example, glycerol, erythritol, arabitol, sorbitol, mannitol, glucose, fructose, sucrose and trehalose; polymer compounds such as, but not limited to, dextrans, levans, and polyethylene glycols; and amino acids and derivatives thereof, such as glycine, alanine, proline, octopine, sarcosine, etc. In addition, certain ionic stabilizing compounds, including, for example, citrates, sulfates, acetates, phosphates, and quaternary amines, may be useful to practice the invention.

A buffer containing a stabilizing agent is prepared which comprises, for example, from about 50 mM to about 150 mM TRIS, pH 7.4, from about 0.1% to about 1.0% (w/v) BSA, and from about 1% to about 10% (w/v) of a stabilizing agent. For example, sucrose or trehalose can be used as the stabilizing agent. The quenched soluble fibrin solution is diluted with this buffer to a final concentration of soluble fibrin polymers of from about 0.1 to about 1.0 mg/ml. The resulting polymer solution is then lyophilized by standard procedures.

The lyophilized preparation is preferably stored at 2° C. to 8° C. The lyophilized preparation is easily reconstituted in water, preferably in deionized or distilled water, and is further diluted, preferably in a physiological buffer at physiological pH, e.g., pH 7–8, as required. For example, the lyophilized preparation may be reconstituted in a small volume of water and then further diluted in the buffer containing the stabilizing agent used above. The reconstituted preparation represents the stabilized fibrin polymer composition of the invention, which may be beneficially used as an immunogen to raise fibrin-specific antibodies.

FIG. 1 represents a stability study of the stabilized fibrin polymer composition of the invention prepared using the stabilization buffer described above, which comprised 5% (w/v) sucrose, which was reconstituted after lyophilization with Milli-Q water to 400 µg/ml, further diluted to 40 µg/ml in a buffer comprising 100 mM Tris, 0.5% (w/v) BSA, and 5% (w/v) sucrose, at pH 7.4, stored at 4° C., 22° C. or 37° C. for varying lengths of time, and tested for immunoreactivity against MH1 using a standard ELISA format on days 1, 2, 3, 4, 7 and 14 post-reconstitution.

FIG. 1 indicates that the stabilized fibrin polymer composition of the invention retains substantial immunoreactivity after reconstitution for up to 14 days post-reconstitution, whether the reconstituted composition was stored at 4° C., 22° C. (RT), or 37° C.

The stabilized fibrin polymer composition of the invention in the lyophilized form retains its immunoreactivity for at least 6 months when stored at 4° C.

The increased immunoreactive stability of the fibrin polymer composition indicates that this composition will serve as a superior immunogen for raising fibrin-specific antibodies.

5.2. PRODUCTION OF MONOCLONAL ANTIBODIES

A fibrin-specific antibody is an antibody capable of specifically recognizing soluble crosslinked DesAABB fibrin polymers and soluble non-crosslinked DesAABB fibrin polymers, but which does not specifically bind to: (a) fibrinogen, (b) plasmin-derived fibrinogen degradation products, (c) DesAA fibrin monomers, (d) DesAA fibrin polymers, (e) DesAABB fibrin monomers, (f) crosslinked fibrinogen, (g) DesAA fibrin monomer-fibrinogen complex, and (h) plasmin-derived fibrin degradation products.

Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above, and each can be in isolated form. Such antibodies may be used, for example, in the detection of soluble crosslinked DesAABB fibrin polymers and soluble non-crosslinked DesAABB fibrin polymers in a biological sample, including, but not limited to, blood plasma and serum. Alternatively the antibodies may be used in a method to image fibrin clots or to deliver thrombolytic or cytotoxic agents to the sites of fibrin deposition in vivo. Thus, such antibodies may be utilized as part of thrombotic disease treatment methods, and/or may be used as part of diagnostic techniques whereby patients may be tested for abnormal levels of soluble crosslinked DesAABB fibrin polymers and soluble non-crosslinked DesAABB fibrin polymers. Furthermore, such antibodies may be utilized to evaluate predisposition for a thrombotic event, support a diagnosis of a thrombotic event, or monitor a thrombotic event in a mammal, comprising detecting the presence or amount of soluble crosslinked DesAABB fibrin polymers and soluble non-crosslinked DesAABB fibrin polymers in a sample from said mammal, and comparing said amount to a control sample.

Polyclonal antibodies are heterogeneous populations of antibody molecules derived from the sera of animals immunized with an antigen. For the production of polyclonal antibodies, host animals may be immunized by injection with the immunogen of the invention, supplemented with adjuvants as described below.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature, 256:495–497; and U.S. Pat. No. 4,376,110), the human B-cell hybridoma technique (Kosbor et al., 1983, Immunology Today, 4:72; Cole et al., 1983, Proc. Natl. Acad. Sci. USA, 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science, 242:423–426; Huston et al., 1988, Proc. Natl. Acad. Sci. USA, 85:5879–5883; and Ward et al., 1989, Nature, 334:544–546) can be adapted to produce single chain antibodies against soluble crosslinked DesAABB fibrin polymers and soluble non-crosslinked DesAABB fibrin polymers. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

5.2.1. USE OF ANTIGEN-FREE ANIMALS

The present method encompasses the production of fibrin-specific antibodies using germfree and antigen-free (AF) animals. However, the present method also contemplates that the improved stability of the composition comprising the immunogen of the invention will also allow for the production of fibrin-specific antibodies from non-germfree and non-AF animals.

Production of fibrin-specific antibodies from germfree or antigen-free (AF) animals is carried out by any method known in the art. See, for example, Wostmann, B. S., [ed.], Gnotobiotes: Standards and Guidelines for the Breeding, Care and Management of Laboratory Animals, National Research Council, National Academy of Sciences, Washington, D.C. 1970; Coates, M. E., et al., The Germfree Animal in Research, Academic Press, London, 1968; and Pleasants, J. R., Gnotobiotics, in: Handbook of Laboratory Animal Science, Vol. 1, Melby, E. C., et al., [eds.], CRC Press, Boca Raton, Fla., 117, (1974), the disclosures of which are incorporated herein in their entirety by reference. See also U.S. Pat. Nos. 5,091,512; 5,120,834; and 5,223,410, the disclosures of which are incorporated in their entirety herein by reference. The following procedure represents one example by which AF animals may handled, maintained, bred, and immunized to produce fibrin-specific monoclonal antibodies.

5.2.2. IMMUNIZATIONS

The present method encompasses the production of fibrin-specific monoclonal antibodies. However, the present method also contemplates that the improved stability of the composition comprising the immunogen of the invention will also allow for the production of fibrin-specific polyclonal antibodies. Polyclonal antibodies derived using the immunogen of the invention can be made by immunizing a germfree or AF animal, or even a non-germfree animal, with the immunogen of the invention as described hereinabove, followed by separating the polyclonal antibodies from the animal by conventional techniques, e.g., by separating the serum from the animal.

For the production of antibodies against soluble crosslinked DesAABB fibrin polymers and soluble non-crosslinked DesAABB fibrin polymers, various host animals may be immunized by injection with the immunogen of the invention. Such host animals may include, but are not limited to, goats, rabbits, chickens, mice, and rats, to name but a few.

Various adjuvants may be used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

One example of the immunization procedure using AF mice is described hereinbelow.

AF mice may be used as the lymphocyte donor in the production of monoclonal antibodies against the immunogen of the invention. Solutions of all antigens are prepared under sterile conditions in a laminar flow hood.

Immunizations are carried out according to any protocol known in the art. The following protocol is but one example of how AF mice may be immunized. The immunogen of the invention (5–50 $\mu$g) is dissolved in physiological buffer and emulsified with an equal volume of Freund's Complete Adjuvant (FCA). Interferon (1000 units) may be added to the solution of antigen prior to the preparation of the emulsion. Sterile syringes and needles are used for all immunizations. The syringes are transferred to the AF isolator via the entry port where they are sterilized by spraying with a solution of peracetic acid (2%). Booster injections are given using the same amount of antigen and the replacement of FCA with Freund's Incomplete Adjuvant. A total of three booster immunizations are given each at intervals of three weeks. The final boost (without adjuvant) is given 3–4 days prior to fusion. All immunizations are given intraperitoneally. The mice are removed from the isolator on the day of the fusion and are immediately sacrificed by $CO_2$ asphyxiation. The spleens are removed and the splenocytes fused with mouse myeloma cells (NS1) using standard hybridoma technology.

The spleen cells from the immunized mice are fused with a fusagent such as, for example, polyethylene glycol 4000 (3000–3700). The cells are incubated in HAT selection media in T flasks for 1 week. After this time, the cells may be plated out into, for example, 5×96 well plates.

Positive clones are then selected that produce antibodies that recognize the immunogen, but do not crossreact with (a) fibrinogen, (b) plasmin-derived fibrinogen degradation products, (c) DesAA fibrin monomers, (d) DesAA fibrin polymers, (e) DesAABB fibrin monomers, (f) crosslinked fibrinogen, (g) DesAA fibrin monomer-fibrinogen complex, and (h) plasmin-derived fibrin degradation products, according to any method of detection known in the art (see below). Once each promising cell line is stabilized, it is weaned onto a serum-free medium.

5.2.3. DETECTION OF FIBRIN-SPECIFIC ANTIBODY

Qualitative and quantitative determinations of monoclonal antibody may be performed using any technique known in the art. For example, qualitative and quantitative determinations of monoclonal antibody may be performed using an enzyme linked immunosorbent assay (ELISA). An ELISA may be performed using human fibrin immobilized onto a 96 well PVC plate (Costar). The fibrin coated assay plates may be prepared by incubating 100 μL of a fibrinogen solution (Kabi, grade L) (50 μg/mL borate/saline buffer) overnight at 4° C. Unbound fibrinogen was removed by washing with PBS containing 0.05% TWEEN™ 80 dispersant (PBS-TWEEN). The fibrinogen coated onto each plastic well is converted to fibrin by incubation with 100 μL of a thrombin solution (10 NIH units/ml) containing 2 mM $CaCl_2$ for 1 hr at 37° C. Standard calibration curves for the antibody may be constructed using a preparation of antibody which is homogeneous by SDS-PAGE.

To prevent non-specific binding, the fibrin coated plates may be incubated with a 1% solution of BSA in PBS pH7.4. Antibody containing solutions (100 μL) may then be added and incubated at 37° C. for 90 min. After each step in the procedure the wells are extensively washed with PBS-TWEEN™ dispersant. Bound antibody is detected by the addition of a 1000 fold dilution of rabbit anti-mouse antibody conjugated, for example, to alkaline phosphatase (Sigma) diluted in PBS, 1% BSA pH 8.0.

In addition, an initial screening may be carried out to select fibrin-specific antibodies that bind to epitopes other than the epitope recognized by monoclonal antibody MH-1. For example, an affinity column may be prepared by coupling MH1 to a SEPHAROSE™ gel column. Such an MH1 affinity column may be prepared by the coupling of MH1 antibody to cyanogen bromide activated SEPHAROSE™ 4B gel (Pharmacia) as is known in the art. See Pharmacia product insert for methods for preparing an antibody-SEPHAROSE™ 4B gel column using preactivated SEPHAROSE™ 4B gel. Soluble crosslinked DesAABB fibrin polymers and soluble non-crosslinked DesAABB fibrin polymers can then be prepared by addition of low levels of thrombin to citrated plasma. After quenching of the thrombin activity by addition of a potent thrombin inhibitor such as hirudin, the plasma samples may be applied to the SEPHAROSE™ gel-MH1 column. The soluble fibrin is then applied to the SEPHAROSE™ gel-MH1 column in the presence of phosphate buffered saline (PBS). After binding to the SEPHAROSE™ gel-MH1 column, the bound soluble fibrin polymers can be used to capture other fibrin-specific monoclonal antibodies than bind to fibrin at epitopes other than the epitope recognized by MH1. Any antibody that binds to the soluble fibrin polymers adhered to the affinity column can then be eluted and assayed to determine whether it meets the requirements of a fibrin-specific antibody, i.e., that it does not specifically bind to: (a) fibrinogen, (b) plasmin-derived fibrinogen degradation products, (c) DesAA fibrin monomers, (d) DesAA fibrin polymers, (e) DesAABB fibrin monomers, (f) crosslinked fibrinogen, (g) DesAA fibrin monomer-fibrinogen complex, and (h) plasmin-derived fibrin degradation products.

5.2.4. PURIFICATION OF FIBRIN-SPECIFIC MONOCLONAL ANTIBODY

Purification of a monoclonal antibody may be carried out by any method known in the art. The following description is but one non-limiting example of a method to purify a monoclonal antibody.

Before purification, 4 liter batches of tissue culture supernatants are centrifuged to remove cellular debris and filtered through a 0.8 micron nylon membrane to remove any residual particulate material. The hybridoma supernatant is concentrated at 4° C. to a volume of 500 mL using a spiral wound ultrafiltration system employing a YM type membrane (Amicon) with molecular weight cut off of 30,000. Buffer exchange to 20 mM 2(N-morpholine) ethane sulphonic acid (MES), pH 6 (Buffer A) is accomplished by diafiltration according to the manufacturers instructions. After further concentration to a final volume of 100 ml, the antibody solution is filtered through a 0.451 micron nylon membrane before further purification. The concentrated antibody solution is purified by liquid chromatography on a Waters HPLC chromatograph using a 7.75 mm×10 cm ABX column (J. T. Baker, Phillipsburg, N.J.). The column is equilibrated with buffer A and the sample (100 ml) is applied at a flow rate of 1.0 ml/min. After extensive washing with buffer A, the antibody is eluted from the column with a gradient from buffer A to 100% buffer B (1M sodium acetate pH7) at 1 ml/min. Fractions (2 ml) are collected and those containing MAb (as determined by ELISA) are pooled and dialyzed against phosphate buffer saline (PBS) (20 mM sodium phosphate, 150 mM sodium chloride, pH7.4) and stored at −20° C. at concentrations >1 mg/ml. The ABX column may be regenerated by washing for 5 minutes with 100% buffer B, followed by re-equilibration with 15 column volumes of buffer A.

5.3. DETERMINATION OF FIBRIN SPECIFICITY

Initial determination of fibrin specificity may be achieved by any technique known in the art. For example, hybridoma supernatants may be screened separately on fibrin and fibrinogen coated microtiter plates. Only those cell lines producing antibody that do not crossreact with fibrinogen are accepted.

Further confirmation of fibrin specificity may be determined utilizing a competition assay with fibrinogen in solution, thereby confirming that the antibody does not recognize fibrinogen in solution.

The competition assay employed to ascertain the fibrin specificity of the antibody may be performed as described for the ELISA assay hereinabove with preincubation of the antibody with fibrinogen in solution. Briefly, hybridoma supernatant may be incubated at 37° C. for 30 minutes with solutions of fibrinogen at physiological concentrations (4 mg/ml) containing BSA (10 mg/ml) to prevent non specific binding of antibody to fibrinogen. The fibrinogen/antibody solution is then transferred to wells of a microtiter plate which had been coated with fibrin. GlyProArgPro (GPRP) may be added to the fibrinogen inhibitor to prevent possible polymerization of fibrinogen by residual thrombin in the fibrin wells. The assay is then performed as a conventional ELISA assay for antibody bound to an immobilized antigen. In all experiments to test the fibrin specificity of an antibody a second antibody such as, for example, 45J produced by hybridoma ATCC HB 9740, may be used as a control. Monoclonal antibody 45J crossreacts with fibrin and fibrinogen.

5.4. PREPARATION OF COLUMNS FOR AFFINITY CHROMATOGRAPHY

SEPHAROSE™ gel-MH1 columns may be prepared as follows:

1 g of freeze dried cyanogen bromide activated SEPHAROSE™ 4B gel (Pharmacia) is weighed out and suspended in 1 mM HCl. The swollen gel is washed for 15 min. in 1 mM HCl on a sintered glass filter.

MH1 antibody (20 mg) is dissolved in coupling buffer (0.1M NaHCO$_3$, pH 8.3 containing 0.5M NaCl) and gently mixed with the swollen gel in a stoppered vessel for 2 hrs. at room temperature or overnight at 4° C.

After mixing, the gel is washed with coupling buffer to remove excess antibody. Unblocked active sites are blocked by treating with 0.1M Tris HCl, pH 8.0 (or 1M ethanolamine, pH 9.0) for 2 hrs. at room temperature. The antibody-bound gel is then washed 3×with 0.1M acetate buffer (pH 4.0 containing 0.5M NaCl) followed by Tris buffer (0.1M, pH 8.0 containing NaCl 0.5M). Coupled antibody may be stored at 4° C. in sodium azide solution (0.05%).

SEPHAROSE™ gel-DesAABB fibrin monomer columns are prepared as follows: DesAABB fibrin monomers are coupled to cyanogen bromide-activated SEPHAROSE™ 4B gel in the presence of 1M NaBr in 0.1M borate buffer (pH 8.2) using the procedure described above for preparation of SEPHAROSE™ gel-MH1.

5.5. CHARACTERIZATION OF THE SOLUBLE FIBRIN ENTITY RECOGNIZED BY ANTIBODIES OF THE INVENTION

Evidence that the antibody of the invention only recognizes the polymeric structure of DesAABB fibrin and does not recognize the monomeric desAABB fibrin entity may be obtained by affinity chromatography. Briefly, 0.5 mg of the antibody may be passaged over a 5 ml SEPHAROSE™ gel-desAABB fibrin monomer column. The column is washed with equilibration buffer (0.1M Tris buffered saline (TBS), pH 8.5). The amount of binding to the column is determined. Antibodies are selected that show no significant binding of the antibody to the column. The column may be eluted with 6M guanidine hydrochloride. Protein may be detected by monitoring all fractions at 280 nm. Antibody may be determined by testing immunoreactivity of the protein by means of a solid phase ELISA using fibrin coated microtiter wells. See above for description of the ELISA used. To demonstrate that the SEPHAROSEM gel-desAABB fibrin monomer column is capable of binding an antibody, a fibrinogen specific monoclonal antibody (Mab) is passaged over the column in a control experiment.

Evidence that the antibody of the invention recognizes both crosslinked and non-crosslinked soluble DesAABB fibrin polymers is obtained in an experiment in which soluble DesAABB fibrin polymers are generated by addition of thrombin to citrated plasma samples in the presence and absence of EDTA (EDTA prevents factor XIIIa from crosslinking DesAABB fibrin polymers). The crosslinked and non-crosslinked soluble DesAABB fibrin polymers are prepared as described above and their respective immunoreactivities are measured using the ELISA as described above.

Evidence that the antibody of the invention does not recognize soluble DesAA fibrin polymer may be obtained in an experiment wherein DesAA fibrin polymer is prepared by treating fibrinogen or plasma with the snake venom derived enzyme Batroxobin, from *Bothrops atrox*, which selectively cleaves fibrinopeptide A (FPA) from the fibrinogen molecule. Batroxobin does not cleave fibrinopeptide B (FPB), in contrast to thrombin which cleaves both FPA and FPB. The removal of FPA results in polymerization of the DesAA fibrin monomer units and the formation of a DesAA fibrin clot.

FIG. 2 demonstrates clot formation, as measured by absorbance of the reaction mixture at 340 nm, when a batroxobin solution is incubated for 15 min. at room temperature with a fibrinogen sample. The absorbance increases gradually with time as the soluble DesAA fibrin polymers increase in length and concentration, until finally the clot is formed.

In the experiment to test for antibody recognition of desAA fibrin, soluble desAA fibrin polymer is generated in vitro by incubation of a fibrinogen sample with batroxobin (final concentration, 0.5 units/mL) at 37° C. An aliquot is removed from the batroxobin treated sample after 7 minutes and tested in the ELISA assay as described above. Antibodies are selected for which no reactivity is demonstrated.

It can also be determined from this experiment whether the assay system recognizes fibrinogen-DesAA fibrin complex which is another source of soluble fibrin. Clearly the reaction mixture produced in this experiment would contain such "soluble fibrin" entities since the batroxobin produces DesAA fibrin monomers which are free to interact with other desAA monomers or non-digested fibrinogen molecules. Where no reaction is demonstrated in the assay system after addition of batroxobin, the conclusion can be drawn that the assay does not detect these fibrinogen-DesAA fibrin entities.

A positive control may be is composed of DesAABB fibrin polymers formed by treatment of a plasma sample with thrombin and hirudin. Untreated fibrinogen may be added as a negative control.

Soluble fibrin complex can also arise due to Factor XIIIa crosslinking of native fibrinogen molecules to form fibrinogen dimers (Kanaide et al., *J. Lab. Clin. Med.*, 86:574–579 (1975)). Factor XIIIa (FXIIIa) treated fibrinogen is not detected by the assay system.

In this experiment, fibrinogen coated microtiter plates are first treated with thrombin-activated Factor XIIIa for 1½ hours at 37° C. After quenching residual thrombin activity, the antibody is incubated in the Factor XIIIa treated wells and bound antibody is detected by use of anti-mouse alkaline phosphatase conjugate. Bound anti-mouse antibody is detected by the addition of an alkaline phosphatase substrate. The level of antibody bound to the wells is measured by reading the optical density at 405 nm. Where no antibody is bound to the wells, the antibody does not recognize crosslinked fibrinogen structures. As a positive control the fibrinogen coated wells are treated with thrombin to produce DesAABB fibrin polymers and tested for immunoreactivity with MH1 antibody.

Evidence that an antibody produced by the method of the invention does not bind to plasmin-derived fibrin degradation products and plasmin-derived fibrinogen degradation products can be determined by any standard technique. For example, the techniques described in Section 5.5.2. of U.S. Patent No. 5,120,834 to Gargan et al., which demonstrates that the monoclonal antibody MH1 does not bind to such degradation products, can be utilized.

5.6. PURIFICATION OF SOLUBLE FIBRIN POLYMERS POLYMERS FROM PLASMA BY SEPHAROSE™ GEL-MH1 AFFINITY CHROMATOGRAPHY

Soluble fibrin polymers may be prepared from plasma according to the following protocol. A plasma sample is incubated with thrombin (0.025 units ml) for 7 min. at 37° C. The thrombin activity is quenched by the addition of excess hirudin. The reaction mixture is passaged over a SEPHAROSE™ gel-MH1 column. The starting material, the run-through (nonbound material), and the bound protein (purified protein) which protein are eluted using NaSCN (3M) and dialyzed against PBS, and tested for immunoreactivity with MH1 using the ELISA assay as described above. The immunoreactivity of the thrombin treated plasma after quenching with hirudin (Starting Material), of the bound protein after removal from the column and dialysis (Elution), and of the nonbound material (Nonbound) are then determined.

6. USES FOR FIBRIN-SPECIFIC ANTIBODIES

The fibrin-specific antibodies made by the method of the subject invention can be utilized in any technique known or to be developed in the future that utilizes a fibrin-specific antibody, including those described below.

6.1. IN VIVO DIAGNOSTIC AND THERAPEUTIC USES FOR FIBRIN-SPECIFIC ANTIBODIES

6.1.1. VASCULAR DISEASE LOCALIZATION

A major use of fibrin-specific antibodies is in in vivo imaging and therapeutics. The fibrin-specific antibodies produced according to the method of the invention are capable of targeting fibrin clots or aggregation of fibrin in vivo. They can, therefore, be used in humans for localization of possible tissue or vascular damage and for monitoring of vascular diseases. A fibrin-specific monoclonal antibody is particularly preferred for this use because such monoclonal antibody will not bind to fibrinogen, fibrin degradation products and fibrinogen degradation products, thereby reducing background, which permits one to more precisely localize the fibrin clot or aggregation of fibrin.

For this application, it is preferable to use purified monoclonal antibodies. Preferably, purification may be accomplished by HPLC methods. Purification of monoclonal antibodies for human administration may also be accomplished by ammonium sulfate or sodium sulfate precipitation followed by dialysis against saline and filtration sterilization. Alternatively, immunoaffinity chromatography techniques may be used to purify the monoclonal antibodies.

The purified monoclonal antibodies can be labelled with radioactive compounds, for example $^{123}$I, $^{125}$I, $^{131}$I, $^{99}$mTc, $^{111}$In, and administered to a patient intravenously. The antibody also can be labelled with a magnetic probe. NMR can then be utilized to pinpoint the clot. After localization of the antibodies at the clot or fibrin aggregation they can be detected by emission tomographical and radionuclear scanning techniques thereby pinpointing the location of, for example, the thrombus or fibrin encapsulated tumor.

By way of illustration, the purified monoclonal antibody is suspended in an appropriate carrier, e.g., saline, with or without human albumin, at an appropriate dosage and is administered intravenously, e.g., by continuous intravenous infusion over several hours, as in Miller et al. In Hybridomas in Cancer Diagnosis and Therapy (1982), incorporated herein by reference.

6.1.2. TREATMENT OF VASCULAR DISEASE WITH ANTIBODY CONJUGATES

The antibodies of the subject invention can also be used therapeutically. Antibodies with the proper biological properties are useful directly as therapeutic agents. Alternatively, the antibodies can be bound to a toxin to form an immunotoxin or to a radioactive material or drug to form a radiopharmaceutical or pharmaceutical. Methods for producing immunotoxins and radiopharmaceuticals of antibodies are well-known (see, for example, *Cancer Treatment Reports* (1984) 68:317–328).

Alternatively, the monoclonal antibodies of this invention can be used in conjunction with a broad range of pharmaceutical agents including thrombolytic reagents, e.g., t-PA, urokinase streptokinase, and other proteases that are capable of lysing fibrin. Such use is particularly preferred because the fibrin-specific antibodies of the subject invention permit a very efficient use of such reagents because none of the reagent will be lost by binding to fibrinogen, fibrin degradation products or fibrinogen degradation products. For various reviews on the subject, see Bale et al., 1980, *Cancer Research*, 40:2965–297; Ghose and Blair, 1978, *J. Natl. Cancer Inst.*, 61(3):657–676; Gregoriadis, 1977, *Nature*, 265:407–411; Gregoriadis, 1980 *Pharmac. Ther.*, 10:103–108; and Trouet et al., 1980, *Recent Results Cancer Res.*, 75:229–235.

The methods used for binding these agents to the antibody molecule can involve either non-covalent or covalent linkages. Since non-covalent bonds are more likely to be broken before the antibody complex reaches the target site, covalent linkages are preferred. For instance, a carbodiimide bond can be formed between the carboxy groups of the pharmaceutical agent and the amino groups of the antibody molecule. Bifunctional agents such as dialdehydes or imidoesters can be used to link the amino group of a drug to amino groups of the antibody molecule. The Schiff base reaction can be used to link drugs to antibody molecules. This method involves the periodate oxidation of a drug or cytotoxic agent that contains a glycol or hydroxy group, thus forming an aldehyde which is then reacted with the antibody molecule. Attachment occurs via formation of a Schiff base with amino groups of the antibody molecule. Additionally, drugs with reactive sulfhydryl groups have been coupled to antibody molecules.

6.2. IN VITRO DETECTION AND MEASUREMENT OF SOLUBLE FIBRIN

A major use of fibrin-specific antibodies is in an in vitro immunoassay to detect or measure soluble fibrin polymers in a patient sample. Such assays are generally heterogeneous or homogeneous. In a homogeneous immunoassay the immunological reaction usually involves the specific antibody, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels which may be employed include free radicals, fluorescent dyes, enzymes, bacteriophages, coenzymes, and so forth. The major advantage of a homogeneous immunoassay is that the specific antibody need not be separated from the labeled analyte.

In a heterogeneous immunoassay, the reagents are usually the specimen, the specific antibody, and means for producing a detectable signal. The specimen is generally placed on a support, such as a plate or a slide, and contacted with the antibody in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescers, enzymes, and so forth. Exemplary of heterogeneous immunoassays are the radioimmunoassay, immunofluorescence methods, enzyme-linked immunoassays, and the like.

For a more detailed discussion of the above immunoassay techniques, see "Enzyme-Immunoassay," by Edward T. Maggio, CRC Press, Inc., Boca Raton, Fla., 1980. See, also, for example, U.S. Pat. Nos. 3,690,834; 3,791,932; 3,817,837; 3,850,578; 3,853,987; 3,867,517; 3,901,654; 3,935,074; 3,984,533; 3,996,345; and 4,098,876, which listing is not intended to be exhaustive.

It is believed that, in addition to monoclonal antibodies, polyclonal antibodies derived from an animal using the immunogen of the invention also can be utilized in immunoassays and provide an improved result as compared to polyclonal antibodies derived using a conventional immunogen.

6.2.1. BACKGROUND

As described above, the hemostatic mechanism involves a complex sequence of reactions, by which fibrinogen is ultimately converted by thrombin to fibrin. The end result of these reactions is the formation of a thrombus (blood clot). The sequence of reactions may be simply represented by a three step process as follows:

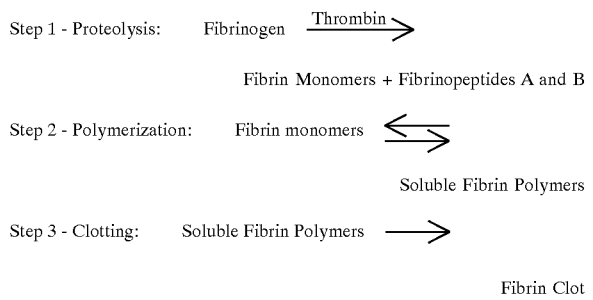

Fibrinogen is composed of three pairs of non-identical polypeptide chains: A$\alpha$, B$\beta$ and $\gamma$. See L. Stryer, *Biochemistry*, Third Edition p. 249, W. H. Freeman and Company New York (1988). In the initial step, whereby fibrinogen is converted to fibrin, shown above as step 1, fibrinogen is cleaved by thrombin to release fibrinopeptide A from the amino-terminal ends of the two fibrinogen A$\alpha$-chains. The resultant monomer is the DesAA fibrin monomer. As also shown above in step 1, simultaneously, but more slowly, thrombin also cleaves fibrinopeptide B from the amino-terminal ends of the two fibrinogen B$\beta$-chains. As a result of the fibrinopeptide release, new amino-terminals are exposed on the fibrin $\alpha$ and $\beta$ chains. As depicted above, the molecules formed in step 1 are fibrinopeptide A, fibrinopeptide B, and the fibrin monomers DesAA fibrin monomer, and DesAABB fibrin monomer, shown above as "fibrin monomers". See W. Nieuwenhuizen, *Blood Coagulation and Fibrinolysis*, 4:93–96 (1993). As shown above in step 2, the fibrin monomers then form both non-covalent (non-crosslinked) and covalent (crosslinked) polymers to form soluble fibrin polymers. As shown above in step 3, the soluble fibrin polymers then form the fibrin clot.

Soluble fibrin is defined as any molecular species originating from fibrinogen or fibrin that can lead to fibrin polymer formation or any fibrin(ogen) derived molecular species which has a molecular weight greater than the molecular weight of native fibrinogen, and is maintained in solution in blood. Non-crosslinked and crosslinked DesAABB fibrin polymers, formed in step 2 above, are two of the several species of soluble fibrin and are also two species of soluble fibrin polymer. Additionally, the term soluble fibrin includes various other species; for example, DesAA fibrin polymers, complexes formed by interactions between fibrin monomers (either DesAA or DesAABB fibrin monomers) and the fibrinogen degradation products X, Y, D and E (see Section 6.1 above for a description of these degradation products) and also, for example, DesAA and DesAABB monomers in complex with fibrinogen, see Nieuwenhuizen, pp. 93–94.

Soluble fibrin polymers are the immediate precursors of the insoluble fibrin, i.e., the clot, and consequently the plasma levels of the soluble fibrin polymers are believed to be elevated in individuals with impending or existing thrombosis (intravascular blood clot formation). The detection and measurement of the amount of these polymers in blood, in particular the DesAABB soluble fibrin polymers would therefore, be useful as an indication of incipient blood clot formation. See Bang and Chang, pp. 119–121; and Nieuwenhuizen, p. 94; and Marder et al., U.S. Pat. No. 5,206,140.

Certain species of soluble fibrin have previously been detected or measured and detected using a variety of methods including, for example, measurement of fibrinopeptide A, measurement by using antibodies to the A$\alpha$ and $\gamma$ epitopes exposed upon conversion of fibrinogen to fibrin, Nieuwenhuizen, pp. 94–96, and measurement of D-dimers, Marder et al., U.S. Pat. No. 5,206,140. Other methods used to detect or measure and detect soluble fibrin include measurement of agglutination of erythrocytes coated with fibrin in the presence of soluble fibrin, gel exclusion chromatography, rate enhancement of plasminogen activation by the plasminogen activator t-PA, see Nieuwenhuizen, at p. 94, ethanol or protamine sulfate gelation, N-terminal analysis of fibrinogen fractions purified from plasma, incorporation of $^{14}$C-labeled glycine-ethyl ester and agarose gel chromatography, see Bang and Chang at pp. 111–118. None of these tests detects and measures specifically both soluble crosslinked and soluble non-crosslinked fibrin polymers.

6.2.2. IN VITRO ASSAY FOR SOLUBLE FIBRIN POLYMERS

The in vitro assay disclosed herein is based upon the discovery that it is possible to produce a fibrin-specific antibody useful to detect and measure the amount of soluble crosslinked DesAABB fibrin polymers and soluble non-crosslinked DesAABB fibrin polymers, which polymers are composed of DesAABB fibrin monomers, in a patient sample and which antibody does not detect (a) fibrinogen, (b) plasmin-derived fibrinogen degradation products, (c) DesAA fibrin monomers, (d) DesAA fibrin polymers, (e)

DesAABB fibrin monomers, (f) crosslinked fibrinogen (Factor XIIIa treated fibrinogen), (g) DesAA fibrin monomer-fibrinogen complexes and (h) plasmin-derived fibrin degradation products ("species (a)–(h)". The fibrinogen degradation products and the fibrin degradation products are those generated by plasmin digestion of fibrinogen or fibrin as described above.

It is believed that the above described assay is particularly useful in the clinical diagnosis of conditions characterized by thrombosis. For example, such antibodies may be utilized to evaluate predisposition for a thrombotic event, support a diagnosis of a thrombotic event, or monitor a thrombotic event in a mammal, comprising detecting the presence or amount of soluble crosslinked DesAABB fibrin polymers and soluble non-crosslinked DesAABB fibrin polymers in a sample from said mammal, and comparing said amount to a control sample.

The assay may be carried out utilizing any suitable sample of body fluid but is preferably done utilizing as a sample mammalian blood. Suitable mammals include for example rabbits, monkeys, and humans with humans being most preferred.

In such in vitro assays, any antibody, known or to be developed, useful to detect soluble crosslinked DesAABB fibrin polymers and soluble non-crosslinked DesAABB fibrin polymers, and which antibody does not detect species (a)–(h) can be utilized. Once detected, the soluble crosslinked DesAABB fibrin polymers and soluble non-crosslinked DesAABB fibrin polymers in a sample can be measured either by comparison to a control sample or by use of standards having known amounts of soluble crosslinked DesAABB fibrin polymers and soluble non-crosslinked DesAABB fibrin polymers.

It is to be noted that two or more antibodies can be used as the means of detection. Thus, antibodies with different specificities can be used in combination to detect and measure soluble crosslinked DesAABB fibrin polymers and soluble non-crosslinked DesAABB fibrin polymers in a sample, wherein for example, neither antibody alone is able to form a complex with both soluble crosslinked DesAABB fibrin polymers and soluble non-crosslinked DesAABB fibrin polymers, whereas the two or more antibodies can form such complexes. Of course, no one antibody can crossreact with species (a)–(h). It is also to be noted that it may be necessary to utilize a species specific antibody.

The antibodies of the present invention may be used in any immunoassay system known in the art including, but not limited to: radioimmunoassays, enzyme-linked immunosorbent assays, "sandwich" assays, precipitin reactions, gel diffusion immunodiffusion assays, agglutination assays, fluorescent immunoassays, protein A immunoassays and immunoelectrophoresis assays, to name but a few. U.S. Pat. No. 4,629,783 and patents cited therein also describe suitable assays.

The antibodies may be used as the basic reagents in a number of different immunoassays to determine the presence of the soluble crosslinked and soluble non-crosslinked DesAABB fibrin polymers in a sample of blood or other body fluid. Generally speaking, the antibodies can be employed in any type of immunoassay, whether qualitative or quantitative. This includes both the two-site sandwich assay and the single site immunoassay of the non-competitive type, as well as traditional competitive binding assays.

Particularly preferred, for ease of detection, and its quantitative nature, is the sandwich or double antibody assay, of which a number of variations exist, all of which are intended to be encompassed by the present invention.

For example, in a typical forward sandwich assay, unlabeled antibody is immobilized on a solid substrate, e.g., microtitre plate wells, and the sample to be tested is brought into contact with the bound molecule. After a suitable period of incubation, for a period of time sufficient to allow formation of an antibody-antigen binary complex, a second antibody, labelled with a reporter molecule capable of inducing a detectable signal, is then added and incubation is continued allowing sufficient time for binding with the antigen at a different site and the formation of a ternary complex of antibody-antigen-labeled antibody. Any unreacted material is washed away, and the presence of the antigen is determined by observation of a signal, which may be quantitated by comparison with control samples (standards) containing known amounts of antigen. Variations on the forward sandwich assay include the simultaneous assay, in which both sample and antibody are added simultaneously to the bound antibody, or a reverse sandwich assay in which the labelled antibody and sample to be tested are first combined, incubated and added to the unlabelled surface bound antibody. These techniques are well known to those skilled in the art, and the possibility of minor variations will be readily apparent. As used herein, "sandwich assay" is intended to encompass all variations on the basic two-site technique.

As a more specific example, in a typical forward sandwich assay, a primary antibody is either covalently or passively bound to a solid support. The solid surface is usually glass or a polymer, the most commonly used polymers being cellulose, polyacrylamide, nylon, polystyrene, polyvinylchloride or polypropylene. The solid supports may be in the form of tubes, beads, discs or microplates, or any other surfaces suitable for conducting an immunoassay. The binding processes are well known in the art. Following binding, the solid phase-antibody complex is washed in preparation for the test sample. An aliquot of the body fluid to be tested is then added to the solid phase complex and incubated for a period of time sufficient to allow binding of any soluble non-crosslinked DesAABB fibrin polymer and soluble crosslinked DesAABB fibrin polymer present to the antibody specific for the above proteins. The second antibody is then added to the solid phase complex and incubated for an additional period of time sufficient to allow the second antibody to bind to the primary antibody-antigen solid phase complex. The second antibody is linked to a reporter molecule, the visible signal of which is used to indicate the binding of the second antibody to any antigen in the sample. By "reporter molecule", as used in the present specification is meant a molecule which by its chemical nature, provides an analytically detectable signal which allows the detection of antigen-bound antibody. Detection must be at least relatively quantifiable, to allow determination of the amount of antigen in the sample, this may be calculated in absolute terms, or may be done in comparison with a standard (or series of standards) containing a known normal level of antigen.

The most commonly used reporter molecules in this type of assay are either enzymes or fluorophores. In the case of an enzyme immunoassay, an enzyme is conjugated to the second antibody, often by means of glutaraldehyde or periodate. As will be readily recognized, however, a wide variety of different conjugation techniques exist, which are well known to the skilled artisan. Commonly used enzymes include horseradish peroxidase, glucose oxidase, β-galactosidase and alkaline phosphatase, among others.

The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. In all cases, the enzyme-labelled antibody is added to the first antibody complex and allowed to bind to the complex, then the excess reagent is washed away. A solution containing the appropriate substrate is then added to the tertiary complex of antibody-antigen-labelled antibody. The substrate reacts with the enzyme linked to the second antibody, giving a qualitative visual signal, which may be further quantitated, usually spectrophotometrically, to give an evaluation of the amount of antigen which is present in the serum sample.

Alternately, fluorescent compounds, such as fluorescein or rhodamine, may be chemically coupled to antibodies without altering their binding capacity. When activated by illumination with light of a particular wavelength, the fluorochrome-labelled antibody absorbs the light energy, inducing a state of excitability in the molecule, followed by emission of the light at a characteristic longer wavelength. The emission appears as a characteristic color visually detectable with a light microscope. As in the enzyme immunoassay (EIA), the fluorescent-labelled antibody is allowed to bind to the first antigen-complex. After washing the unbound reagent, the remaining ternary complex is then exposed to light of the appropriate wavelength, and the fluorescence observed indicates the presence of the antigen. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

Alternatively, the sample to be tested, either mammalian blood or other body fluid containing the soluble non-crosslinked fibrin DesAABB polymer and the soluble crosslinked DesAABB fibrin polymer may be used in a single site immunoassay wherein it is adhered to a solid substrate either covalently or noncovalently. An unlabeled antibody is brought into contact with the sample bound on the solid substrate. After a suitable period of incubation, for a period of time sufficient to allow formation of an antibody-antigen binary complex a second antibody, labelled with a reporter molecule capable of inducing a detectable signal, is then added and incubation is continued allowing sufficient time for the formation of a ternary complex of antigen-antibody-labeled antibody. For the single site immunoassay, the second antibody may be a general antibody (i.e., xenogeneic antibody to immunoglobulin, particularly anti-(IgM and IgG) linked to a reporter molecule) that is capable of binding an antibody that is specific for the soluble crosslinked fibrin polymer and the soluble non-crosslinked fibrin polymer.

The detection and measurement of soluble non-crosslinked DesAABB fibrin polymers and soluble crosslinked DesAABB fibrin polymers in vitro is particularly useful when such detection and measurement is done, using the plasma of patients, to obtain an indication of an impending or existing thrombotic event, said event being due to an impending or existing thrombosis. See, e.g., W. Nieuwenhuizen, p. 94, Bang and Chang, pp. 109–122, and Marder et al., U.S. Pat. No. 5,206,140. Such events include, for example, deep vein thrombosis ("DVT"), a condition which arises as a result of blood clot formation in the deep veins of the leg; pulmonary embolism (PE), which arises when a thrombus (blood clot) becomes dislodged from the deep veins and embolizes to the pulmonary vasculature; disseminated intravascular coagulation which arises as a result of systemic activation of the blood clotting cascade, e.g., in bacterial infection; myocardial infarction (MI), which arises as a result of a thrombus occluding the coronary arteries which supply blood to the heart muscle; stroke; and intracardiac thrombi formed as a result of atrial fibrillation. The type of thrombotic event can be diagnosed by use of the assay for detection and measurement of soluble non-crosslinked DesAABB fibrin polymers and soluble crosslinked DesAABB fibrin polymers in combination with observation of other patient symptoms. The symptoms utilized are those which would be commonly utilized in clinical diagnosis of an impending thrombotic event. For example, said detection and measurement of soluble DesAABB fibrin polymers is particularly useful as a means of differentially diagnosing patients with chest pain due to impending MI from patients with chest pain due to other conditions.

Soluble fibrin may detected in fresh or frozen plasma samples using a sandwich type enzyme-linked immunoassay system. The capture antibody is any fibrin-specific antibody produced according to the method of the present invention. The detection (tag) antibody may be a HRP conjugate of the same antibody. Alternatively, a HRP conjugate of the anti-fibrinogen antibody 45J, could be employed as the tagging antibody.

7. KITS FOR IN VITRO DETECTION OF SOLUBLE FIBRIN POLYMERS

It is to be understood that the present invention is not limited to the use of monoclonal antibodies in the assay. However, where such antibody is used, with respect to the kit hereinafter described, these kits contain a set of standards, a first antibody (i.e., capture antibody, for example MH1) which can be immobilized on a surface and a second antibody labeled with a signal generator as described above. These kits contain standards or calibrators in the form of known amounts of soluble cross-linked DesAABB fibrin polymer and soluble non-crosslinked DesAABB fibrin polymer. Such standards or calibrators may be prepared by the isolation of soluble crosslinked and soluble non-crosslinked DesAABB fibrin polymers using the MH1-SEPHAROSE™ gel affinity column as described above. The kits may also contain specific buffers, separating agents and other controls. The kits may contain collection devices or chemicals to treat the sample to be assayed.

All publications and patents cited above are herein incorporated by reference.

We claim:

1. A method for the production of a fibrin-specific antibody comprising immunizing an animal with a composition comprising soluble crosslinked DesAABB fibrin polymers and soluble non-crosslinked DesAABB fibrin polymers and selecting an antibody which specifically binds to soluble crosslinked DesAABB fibrin polymers and soluble non-crosslinked DesAABB fibrin polymers, but which does not crossreact with (a) fibrinogen, (b) plasmin-derived fibrinogen degradation products, (c) DesAA fibrin monomers, (d) DesAA fibrin polymers, (e) DesAABB fibrin monomers, (f) crosslinked fibrinogen, (g) DesAA fibrin monomer-fibrinogen complex, and (h) plasmin-derived fibrin degradation products.

2. The method of claim 1 which further comprises:
(a) removing from said animal cells that are capable of producing an antibody;
(b) fusing said cells with immortalizing cell to form a continuous hybridoma cell line; and
(c) screening said continuous hybridoma cell line to select a continuous hybridoma cell line that produces said fibrin-specific antibody.

3. The method of claim 1 wherein said animal is selected from the group consisting of a goat, a rabbit, a chicken, a mouse and a rat.

4. The method of claim 1 wherein said animal is an antigen-free animal or a germ-free animal.

5. The method of claim 4 wherein said antigen-free animal or said germ-free animal is a mouse.

6. The method of claim 5 wherein said mouse is a Balb/C mouse.

7. The method of claim 1 which further comprises separating serum from said animal.

8. A method for the production of a fibrin-specific antibody comprising immunizing an animal with a composition comprising soluble crosslinked DesAABB fibrin polymers and soluble non-crosslinked DesAABB fibrin polymers and a stabilizing agent and selecting an antibody which specifically binds to soluble crosslinked DesAABB fibrin polymers and soluble non-crosslinked DesAABB fibrin polymers, but which does not crossreact with (a) fibrinogen, (b) plasmin-derived fibrinogen degradation products, (c) DesAA fibrin monomers, (d) DesAA fibrin polymers, (e) DesAABB fibrin monomers, (f) crosslinked fibrinogen, (g) DesAA fibrin monomer-fibrinogen complex, and (h) plasmin-derived fibrin degradation products.

9. A continuous hybridoma cell line which produces a fibrin-specific monoclonal antibody that specifically binds to soluble crosslinked DesAABB fibrin polymers and soluble non-crosslinked DesAABB fibrin polymers, but which does not specifically bind to: (a) fibrinogen, (b) plasmin-derived fibrinogen degradation products, (c) DesAA fibrin monomers, (d) DesAA fibrin polymers, (e) DesAABB fibrin monomers, (f) crosslinked fibrinogen. (g) DesAA fibrin monomer-fibrinogen complex, and (h) plasmin-derived fibrin degradation products, with the proviso that said monoclonal antibody is not MH1 or does not bind to the epitope recognized by MH1.

10. The continuous hybridoma cell line of claim 9 wherein said fibrin-specific monoclonal antibody does not bind to the epitope recognized by MH1 or does not bind to the epitope recognized by MH1.

11. A fibrin-specific antibody that specifically binds to soluble crosslinked DesAABB fibrin polymers and soluble non-crosslinked DesAABB fibrin polymers, but which does not specifically bind to: (a) fibrinogen, (b) plasmin-derived fibrinogen degradation products, (c) DesAA fibrin monomers, (d) DesAA fibrin polymers, (e) DesAABB fibrin monomers, (f) crosslinked fibrinogen, (g) DesAA fibrin monomer-fibrinogen complex, and (h) plasmin-derived fibrin degradation products, or an epitope-binding fragment thereof, with the proviso that said antibody is not MH1 or does not bind to the epitope recognized by MH1.

12. The fibrin-specific antibody of claim 11 wherein said antibody is selected from the group consisting of an antibody produced by a continuous hybridoma cell line, a humanized antibody, a chimeric antibody, a single chain antibody and said epitope-binding fragment thereof is selected from the group consisting of an Fab fragment and f(ab')$_2$ fragment.

* * * * *